United States Patent [19]
Jensen et al.

[11] Patent Number: 5,270,306
[45] Date of Patent: Dec. 14, 1993

[54] METHOD OF ANTAGONIZING EXCITATORY AMINO ACIDS BY ADMINISTRATION OF IMIDAZOBENZODIAZEPINE COMPOUNDS

[75] Inventors: Leif H. Jensen, Copenhagen; Jørgen Drejer, Vaerløse; Frank Wätjen, Copenhagen, all of Denmark

[73] Assignee: NeuroSearch A/S, Glostrup, Denmark

[21] Appl. No.: 703,160

[22] Filed: May 20, 1991

Related U.S. Application Data

[63] Continuation-in-part of Ser. No. 509,284, Apr. 13, 1990, abandoned.

[51] Int. Cl.$^5$ .................... A01N 43/62; A61K 31/55
[52] U.S. Cl. ..................................... 514/220
[58] Field of Search ........................ 514/220

[56] References Cited

PUBLICATIONS

De Bonnel et al., Eu J Pharmacology, 93 (1983) 45–54.
Jensen, et al., Life Sciences 33, 393–399 (1983).
Robinson and Coyle, "Glutamate and related acidic excitatory neurotransmitters", FASEB, J., vol. 1, pp. 446–455 (1987).
Krogsgaard-Larsen, "Amino Acid Receptors", Comprehensive Medicinal Chemistry, vol. 3, pp. 493–537, Pergamon Press (1990).

*Primary Examiner*—Marianne M. Cintins
*Assistant Examiner*—Rebecca Cook
*Attorney, Agent, or Firm*—Gordon W. Hueschen

[57] ABSTRACT

A method of antagonizing the biological effects of an excitatory amino acid of a subject in need of such antagonization comprising the step of administering to said subject an effective amount of a compound having the formula

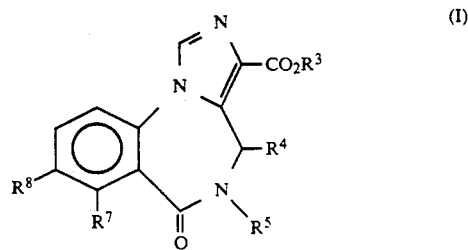

wherein
$R^3$ is hydrogen, $C_{1-8}$-alkyl which may be branched, or cycloalkylmethyl;
$R^7$ and $R^8$ are independently hydrogen, halogen, $CF_3$, CN, $NO_2$, $NH_2$, $C_{1-4}$-alkyl or $C_{1-4}$-alkoxy; and
$R^4$ is hydrogen and $R^5$ is hydrogen or $C_{1-7}$-alkyl; or $R^4$ and $R^5$ together signify $(CH_2)_n$ wherein n is an integer of 2–3.

7 Claims, No Drawings

METHOD OF ANTAGONIZING EXCITATORY AMINO ACIDS BY ADMINISTRATION OF IMIDAZOBENZODIAZEPINE COMPOUNDS

This application is a continutaion-in-part of our prior-filed copending application Ser. No. 07/509,284, filed Apr. 13, 1990, now abandoned.

The present invention relates to a novel treatment with benzodiazepine compounds.

OBJECT

It is an object of the present invention to provide a novel treatment of conditions sensitive to the excitatory amino acids by administration of a benzodiazepine compound to a mammal. This comprises a method of antagonizing the biological effects of an excitatory amino acid of a subject in need of such antagonization, and more particularly a method of antagonizing the biological effects of glutamate of a subject in need of such antagonization.

BACKGROUND OF THE INVENTION

U.S. Pat. No. 4,316,839; U.S. Pat. No. 4,352,817; U.S. Pat. No. 4,386,028; U.S. Pat. No. 4,352,816; U.S. Pat. No. 4,352,818; U.S. Pat. No. 4,353,827; and U.S. Pat. No. 4,489,003 disclose the compounds used for the novel treatment of the present invention. In above U.S. patents the compounds are disclosed as benzodiazepine receptor ligands with antagonistic to agonistic intrinsic activity at the benzodiazepine receptor site, as well as chemical intermediates for such compounds.

Guy de Bonnel et al. in European Journal of Pharmacology 93. 45–54 (1983) disclose that two benzodiazepine (lorazepam and diazepam) agonists selectively antagonize the excitatory activation produced by kainate (an excitatory amino acid (EAA) agonist). However, it is clearly demonstrated therein that the effects of lorazepam and diazepam are benzodiazepine effects which can be antagonized by benzodiazepine receptor antagonists. One of the compounds of formula I below, namely Ro 15-1788 which is identical to the first compound of the table below, was used by Bonnel et al. to demonstrate that the reversal of the excitatory activation produced by kainate was actually mediated through the benzodiazepine receptors rather than through an EAA receptor. Ro 15-1788 is disclosed by Bonnel et al. to antagonize the kainate antagonist response produced by lorazepam and diazepam, as mediated through the benzodiazepine receptor.

The excitatory amino acid receptors (EAA receptors) and their clinical importance are well described (for example Povl Krogsgaard-Larsen, Amino Acid Receptors in Comprehensive Medicinal Chemistry edited by Corwin Hansch et al., Pergamon Press 1990, Vol. 3, p. 493–537 and Michael B. Robinson and Joseph T. Coyle, FASEB J. 1, 446–455 (1987). It is generally recognized that glutamate is an endogenous ligand for all subtypes of EAA receptors, and that aspartate probably also acts as a neurotransmitter for all types of such receptors so far detected. Quisqualate/AMPA (AMPA is α-amino-3-hydroxy-5-methylsoxazole-4-propionate) receptors, NMDA (NMDA is N-methyl-D-aspartate) receptors and kainate receptors for examples are recognized as EAA or glutamate subreceptors. Compounds that act unselectively at all subreceptor types are known, and compounds that act more selectively at one or two subreceptor types are known. Among the clinical diseases which may be treated by administration of EAA antagonists Huntington's disease, Alzheimer's disease, psychosis, and schizophrenia can be mentioned. Further the neurodegenerative events following anoxia, ischemia, migraine and epilepsia may be mentioned.

SUMMARY OF THE INVENTION

The benzodiazepine compounds useful in the treatment provided herewith have the formula I

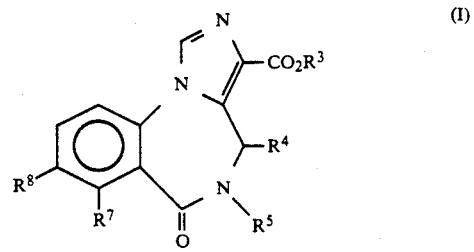

wherein
R is hydrogen, $C_{1-8}$-alkyl which may be branched, or cycloalkylmethyl;
$R^7$ and $R^8$ are independently hydrogen, halogen, $CF_3$, CN, $NO_2$, $NH_2$, $C_{1-4}$-alkyl or $C_{1-4}$-alkoxy; and
$R^4$ is hydrogen and $R^5$ is hydrogen or $C_{1-7}$-alkyl; or $R^4$ and $R^5$ together signify $(CH_2)_n$ wherein n is an integer of 2–3.

Examples of compounds having the formula above are for example:
Ethyl 7-fluor-5,6-dihydro-5-methyl-6-oxo-4H-imidazo[1,5-a][1,4]benzodiazepine-3-carboxylate,
Ethyl 7-chlor-5,6-diydro-5-methyl-6-oxo-4H-imidazo[1,5-a][1,4]benzodiazepine-3-carboxylate,
Ethyl (S)-8-chlor-11,12,13,13a-tetrahydro-9-oxo-9H-imidazo[1,5-a]pyrrolo[2,1-c][1,4]benzodiazepine-1-carboxylate,
Ethyl (R,S)-11,13a-dihydro-9-oxo-9H-imidazo[1,5-a]pyrrolo[2,1-c][1,4]benzodiazepine-1-carboxylate,
Ethyl (R,S)-8-fluor-11,13a-dihydro-9-oxo-9H-imidazo[1,5a]pyrrolo[2,1-c][1,4]benzodiazepine-1-carboxylate,
Ethyl 5,6-dihydro-5-methyl-6-oxo-4H-imidazo[1,5-a][1,4]benzodiazepine-3-carboxylate,
Methyl 5,6-dihydro-5-methyl-6-oxo-4H-imidazo[1,5-a][1,4]benzodiazepine-3-carboxylate,
Isopropyl 5,6-dihydro-5-methyl-6-oxo-4H-imidazo[1,5-a]-[1,4]-benzodiazepine-3-carboxylate,
Methyl 8-fluor-5,6-dihydro-5-methyl-6-oxo-4H-imidazo[1,5a][1,4]benzodiazepine-3-carboxylate,
Isopropyl 8-fluor-5,6-dihydro-5-methyl-6-oxo-4H-imidazo[1,5a][1,4]benzodiazepine-3-carboxylate,
Ethyl 5,6-dihydro-5,7-dimethyl-6-oxo-4H-imidazo[1,5-a][1,4]-benzodiazepine-3-carboxylate,
Ethyl (S)-11,12,13,13a-tetrahydro-9-oxo-9H-imidazo[1,5-a]pyrrolo[2,1-c][1,4]benzodiazepine-1-carboxylate,
Methyl (S)-11,12,13,13a-tetrahydro-9-oxo-9H-imidazo[1,5-a]pyrrolo[2,1-c][1,4]benzodiazepine-1-carboxylate,
Isopropyl (S)-11,12,13,13a-tetrahydro-9-oxo-9H-imidazo[1,5a]pyrrolo[2,1-c][1,4]benzodiazepine-1-carboxylate,
Ethyl (S)-7-fluor-11,12,13,13a-tetrahydro-9-oxo-9H-imidazo[1,5-a]pyrrolo[2,1-a][1,4]benzodiazepine-1-carboxylate, Ethyl (S)-11,12,13,13a-tetrahydro-8-methyl-9-oxo-9H-imidazo[1,5-a]pyrrolo[2,1-a][1,4]benzodiazepine-1-carboxylate, Ethyl 8-fluor-5,6-dihydro-6-oxo-4H-imidazo[1,5-a][1,4]benzodiazepine-3-carboxylate, Ethyl 8-chlor-5,6-dihydro-5-methyl-6-oxo-4H-imidazo[1,5-a][1,4]benzodiazepine-3-carboxylate, Ethyl 8-brom-5,6-dihydro-5-methyl-6-oxo-4H-imidazo[1,5a][1,4]benzodiazepine-3-carboxylate, Ethyl (S)-(+)-7-chlor-11,12,13,13a-tetrahydro-9-oxo-9H-imidazo[1,5-a]pyrrolo[2,1-c][1,4]benzodiazepine-1-carboxylate, Ethyl 5,6-dihydro-5-methyl-8-trifluormethyl-6-oxo-4H-imidazo[1,5-a][1,4]benzodiazepine-3-carboxylate, Ethyl 5,6-dihydro-5-methyl-7-trifluormethyl-6-oxo-4H-imidazo[1,5-a][1,4]benzodiazepine-3-carboxylate, Ethyl 7-chlor-5,6-dihydro-8-fluor-5-methyl-6-oxo-4H-imidazo[1,5-a][1,4]benzodiazepine-3-carboxylate, Ethyl (S)-8-chlor-7-fluor-9-oxo-9H-11,12,13,13a-tetrahydroimidazo[1,5-a]pyrrolo[2,1-c][1,4]benzodiazepine-1-carboxylate, 7-Fluor-5,6-dihydro-5-methyl-6-oxo-4H-imidazo[1,5-a][1,4]-benzodiazepine-3-carboxylate, 7-Chlor-5,6-dihydro-5-methyl-6-oxo-4H-imidazo[1,5-a][1,4]-benzodiazepine-3-carboxylate, (S)-8-Chlor-11,12,13,13a-tetrahydro-9-oxo-9H-imidazo[1,5-a]pyrrolo[2,1-c][1,4]benzodiazepine-1-carboxylate, (R,S)-11,13a-Dihydro-9-oxo-9H-imidazo[1,5-a]-pyrrolo[2,1-c][1,4]benzodiazepine-1-carboxylate;

(R,S)-8-Fluor-11,13a-dihydro-9-oxo-9H-imidazo[1,5a]-pyrrolo[2,1-c][1,4]benzodiazepine-1-carboxylate, 5 6-Dihydro-5-methyl-6-oxo-4H-imidazo[1 5-a][1,4]benzodiazepine-3-carboxylate, 8-Fluor-5,6-dihydro-5-methyl-6-oxo-4H-imidazo[1,5-a][1,4]-benzodiazepine-3-carboxylate, 5,6-Dihydro-5,7-dimethyl-6-oxo-4H-imidazo[1,5-a][1,4]benzodiazepine-3-carboxylate, (S)-11,12,13,13a-Tetrahydro-9-oxo-9H-imidazo[1,5-a]pyrrolo[2,1-c][1,4]benzodiazepine-1-carboxylate, (S)-11,12,13,13a-tetrahydro-9-oxo-9H-imidazo[1,5-a]pyrrolo[2,1-c][1,4]benzodiazepine-1-carboxylate, (S)-7-Fluor-11,12,13,13a-tetrahydro-9-oxo-9H-imidazo[1,5a]pyrrolo[2,1-a][1,4]benzodiazepine-1-carboxylate, (S)-11,12,13,13a-Tetrahydro-8-methyl-9-oxo-9H-imidazo[1,5a]pyrrolo[2,1-a][1,4]benzodiazepine-1-carboxylate.

The compounds can be prepared as described in U.S. Pat. No. 4,316,839; U.S. Pat. No. 4,352,817; U.S. Pat. No. 4,386,028; U.S. Pat. No. 4,352,816; U.S. Pat. No. 4,352,818; U.S. Pat. No. 4,353,827; and U.S. Pat. No. 4,489,003.

It has been found that the compounds of formula I wherein $R^3$ is an ester are metabolized to the corresponding compounds wherein $R^3$ is $CO_2H$, and it has been found that the compounds wherein $R^3$ is $CO_2H$ are more potent than their corresponding ester analogues. Thus it seems highly likely the biological active chemical entities of formula I all are compounds wherein $R^3$ is $CO_2H$. Such compounds have o or very little affinity for the benzodiazepine receptors.

BIOLOGICAL ACTIVITY

The compounds of formula I exhibit valuable biological properties.

For example the compounds exhibit strong pharmacological in vivo ATPA and quisqualate antagonizing effects demonstrating the utility as novel orally bioavailable quisqualate or kainate antagonists, which makes them useful in the treatment of for example psychosis, anoxia, ischemia and migraine.

BIOLOGICAL TESTING

The above mentioned tests are performed as described in more detail below and as based upon the principles also described hereinafter.

ATPA-induced Rigidity

The selective quisqualate receptor agonist ATPA induce rigidity in female NMRI mice (NMRI is a type of mouse developed by the Naval Medical Research Institute and well known to everyone in the art.) at doses between 3 and 15 mg/kg and clonic-tonic seizures ar death, probably due to respiratory arrest, at doses between 15 and 40 mg/kg after intravenous (i.v.) administration.

Method

ATPA ((RS)-α-amino-3-hydroxy-5-tert-butyl-4-isoxazolepropionic acid) was dissolved in distilled water and test compound was dissolved in a polyoxyl 40 hydrogenated castor oil (5% Cremophor RH TM 40 (BASF)).

Test compound was administered either i.v. 5, 30 or 120 min before or p.o. 30 min before an i.v. administration of 15 mg/kg of ATPA to 8 female NMRI mice per dose and the number of mice experiencing rigidity 5 min later was noted. An $ED_{50}$ value was calculated from at least three doses of test compound as the dose inhibiting 50% of the mice from having rigidity.

Quisqualate-induced Clonic Seizures

Quisqualate given icv ("icv" is a route of administration identified as "intracerebral ventricular", from the Latin "Intracerebro ventricular") DBA/2 (DBA/2 is a type of mouse which is identified as a dilute brown agouti. The number 2 designates the second subline. This type of mouse is available from any number of suppliers throughout the world, each of which may or may not add its own acronyms after the number 2, and this strain of mouse was developed by C. C. Little in 1909.) mice induce clonic seizures which can be inhibited by both NMDA and non-NMDA receptor antagonists after icv administration.

Method

Test compound was given i.v. 5 min before a 20 μg icv administration of quisqualate to 10 male DBA/2 mice (weighing 10-12 g) per dose. The number of mice experiencing clonic seizures within the next 2 min was noted. An $ED_{50}$ value was calculated as the dose inhibiting 50% of the mice from having clonic seizures.

The table below presents some data obtained by testing selected compounds.

TABLE

| Compound | ATPA rigidity ED$_{50}$ (mg/kg i.v.) | | Quisqualate induced seizures ED$_{50}$ (mg/kg i.v.) |
|---|---|---|---|
| | 5 min | 30 min | 5 min |
| (F-substituted imidazo-benzodiazepine, R$^3$=CO$_2$CH$_2$CH$_3$) | | 7 | 10 |
| (same, R$^3$=CO$_2$H) | 3 | | |
| (Br-substituted imidazo-benzodiazepine with pyrrolidine, CO$_2$H) | | 10 | |
| (Cl-substituted imidazo-benzodiazepine with azetidine, CO$_2$H) | | 10 | |

Also the compounds of formula I as a secondary result of their EAA-antagonizing properties have been found to antagonize cocaine-induced hypermotility. For example ethyl 8-fluoro-5,6-dihydro-5-methyl-6-oxo-5H-imidazo[1,5-a][1,4]benzodiazepine-3-carboxylate has been found to have an ED$_{50}$ of 1.0 mg/kg administered intra peritoneally.

Principle Cocaine-induced Hypermotility

Quisqualate and kainate administered locally induce an increase in dopamine release in nucleus accumbens and nucleus caudatus accompanied by stereotype behaviour such as hyperlocomotion, rearing, sniffing and grooming. These effects can be inhibited by selective quisqualate antagonists administered locally by the micro-dialyses method.

Also the dopamine uptake inhibitor cocaine administered s.c. induce hypermotility which can be inhibited ay an administration of the glutamage antagonist GDEE (GDEE is glutamate diethylester.) into nucleus accubens.

For these reasons (and others) it has been concluded that non-NMDA receptors regulate the release of dopamine in nucleus accumbens and that non-NMDA receptor antagonists can alleviate the symptoms of psychosis.

Method

Test compound was administered orally or i.p. at doses of 0.1, 1, 10, and 30 mg/kg 30 min before the administration of 25 mg/kg cocaine i.p. to female NMRI mice and the locomotor activity of 2 mice per box was measured for the next 2 hours by use of 8 infrared photobeams per box. The mice had been adapted to the box for at least 16 hours to avoid exploratory motility (neophobia)

Pharmaceutical Compositions

The compounds of formula I. together with a conventional adjuvant, carrier, or diluent, may be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, in the form of suppositories for rectal administration; or in the form of sterile injectable solutions for parenteral (including subcutaneous) use. Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed. Tablets containing ten (10) milligrams of active ingredients or, more broadly, one (1) to one hundred (100) milligrams, per tablet, are accordingly suitable representative unit dosage forms.

Method of Treating

The compounds of formula I are extremely useful in the treatment of central nervous system disorders related to the excitatory amino acids. The compounds of this invention may accordingly be administered to a subject, including a human, in need of treatment, alleviation, or elimination of an indication associated with dysfunctions related to the excitatory amino acids. This includes especially Huntington's disease, Alzheimer's disease, psychosis, anoxia, ischemia and migraine.

We claim:

1. A method of antagonizing the biological effects of glutamate in a subject in need of such antagonization, comprising the step of administering to said subject an effective amount of a compound having the formula

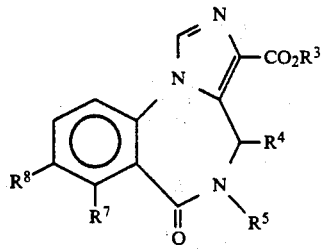
(I)

wherein $R^3$ is hydrogen, $C_{1-8}$-alkyl which may be branched, or cycloalkylmethyl;

$R^7$ and $R^8$ are independently hydrogen, halogen, $CF_3$, CN, $NO_2$, $NH_2$, $C_{1-4}$-alkyl or $C_{1-4}$-alkoxy; and $R^4$ is hydrogen and $R^5$ is hydrogen or $C_{1-7}$-alkyl; or $R^4$ and $R^5$ together signify $(CH_2)_n$ wherein n is an integer of 2-3.

2. A method of antagonizing the biological effects of glutamate of a subject in need of such antagonization, comprising the step of administering to said subject an effective amount of a compound having the formula

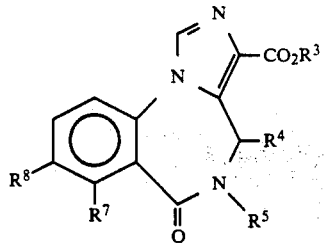
(I)

3. A method according to claim 1 wherein the active ingredient is present together with a pharmaceutically acceptable carrier or diluent.

4. A method according to claim 1 wherein the active ingredient is 8-fluor-5,6-dihydro-5-methyl-6-oxo-4H-imidazo[1,5-a][1,4]benzodiazepine-3-carboxylate.

5. A method according to claim 1 wherein the active ingredient is 8-brom-11,12,13,13a-tetrahydro-9-oxo-9,H-imidazo[1,5-a]pyrrolo[2,1-c][1,4]benzodiazepine-1-carboxylate or an ester thereof.

6. A method according to claim 1 wherein the active ingredient is 12,12a-dihydro-8-chloro-9-oxo-9,H,11H-azeto[2,1-c]imidazo[1,5-a][1,4]benzodiazepine-1-carboxylate.

7. A method according to claim 2 wherein the active ingredient is present together with a pharmaceutically-acceptable carrier or diluent.

* * * * *

UNITED STATES PATENT AND TRADEMARK OFFICE
CERTIFICATE OF CORRECTION

PATENT NO. : 5,270,306　　　　　　　　　　　　　　Page 1 of 2

DATED : December 14, 1993

INVENTOR(S) : Jensen et al.

It is certified that error appears in the above-indentified patent and that said Letters Patent is hereby corrected as shown below:

Col. 1, line 35: "93." should be --93,--
Col. 1, line 58: "1" should be --1--
Col. 1, line 63: "methylsoxazole" should be --methylisoxazole--
Col. 2, line 24: "R" should be --$R^3$--
Col. 3, line 67: "o" should be --no--
Col. 4, line 25: "ar" should be --and--
Col. 4, line 44: "Ouisqualate" should be --Quisqualate--
Col. 4, line 47: Insert after "ventricular")" the word --to--
Col. 5-6, Table: In the third column, the "10" should be moved down one line to be even with the "3" for the second formula.
Col. 5, line 52: "ay" should be --by--
Col. 5, line 52: "glutamage" should be --glutamate--
Col. 5, line 54: "accubens" should be --accumbens--
Col. 8, line 12: Insert the following after the formula: --wherein $R^3$ is hydrogen, $R^7$ and $R^8$ are independently hydrogen, halogen, $CF_3$, CN, $NO_2$, $NH_2$, $C_{1-4}$-alkyl or $C_{1-4}$-alkoxy; and $R^4$ is hydrogen and $R^5$ is hydrogen or $C_{1-7}$-alkyl; or $R^4$ and $R^5$ together signify $(CH_2)_n$ wherein n is an integer of 2-3.--
Col. 8, line 14: Insert a dash after the word "pharmaceutically"
Col. 8, line 21: Delete the comma after "9"
Col. 8, line 24: Delete the comma after the second "9"
Col. 8, line 25: "[2,1-climidazo" should read --[2,1-c]imidazo--

UNITED STATES PATENT AND TRADEMARK OFFICE
CERTIFICATE OF CORRECTION

PATENT NO. : 5,270,306

DATED : December 14, 1993

INVENTOR(S) : Jensen et al.

It is certified that error appears in the above-identified patent and that said Letters Patent is hereby corrected as shown below:

Col. 8, line 26: Insert the words --or an ester thereof-- after the word "boxylate".

Signed and Sealed this

Seventeenth Day of May, 1994

Attest:

BRUCE LEHMAN

Attesting Officer

Commissioner of Patents and Trademarks